(12) United States Patent
Hinze

(10) Patent No.: US 7,651,704 B2
(45) Date of Patent: Jan. 26, 2010

(54) USE OF AN AQUEOUS SOLUTION IN THE TREATMENT OF LIVE ANIMALS

(75) Inventor: Gilbert Theo Hinze, Randburg (ZA)

(73) Assignee: Radical Waters IP (Pty) Ltd. (ZA)

( * ) Notice: Subject to any disclaimer, the term of this patent is extended or adjusted under 35 U.S.C. 154(b) by 384 days.

(21) Appl. No.: 11/652,199

(22) Filed: Jan. 11, 2007

(65) Prior Publication Data
US 2007/0110822 A1    May 17, 2007

Related U.S. Application Data

(63) Continuation of application No. 10/679,449, filed on Oct. 7, 2003, now abandoned, which is a continuation-in-part of application No. 09/529,734, filed as application No. PCT/US98/22372 on Oct. 23, 1998, now abandoned.

(30) Foreign Application Priority Data
Oct. 23, 1997    (ZA)    ..................... 97/9486

(51) Int. Cl.
*A61K 33/00*    (2006.01)
*A61K 33/04*    (2006.01)
*A61K 33/14*    (2006.01)
*A61K 33/40*    (2006.01)
*A01N 59/00*    (2006.01)
*A01N 59/02*    (2006.01)
*A01N 59/08*    (2006.01)
*A61L 2/18*     (2006.01)

(52) U.S. Cl. ................ 424/616; 424/600; 424/613; 424/661; 424/663; 424/665

(58) Field of Classification Search ............ 424/661, 424/600, 613, 663, 665
See application file for complete search history.

(56) References Cited

U.S. PATENT DOCUMENTS 3,616,355 A    10/1971    Themy et al.
5,427,667 A    6/1995     Bakhir et al.
5,540,819 A    7/1996     Bakhir et al.
5,628,888 A    5/1997     Bakhir et al.
5,635,040 A    6/1997     Bakhir et al.
5,674,537 A    10/1997    Morrow
5,871,623 A    2/1999     Bakhir et al.
5,985,110 A    11/1999    Bakhir et al.
2004/0081705 A1*    4/2004    Gotou ..................... 424/600

FOREIGN PATENT DOCUMENTS

BR    9201704 A    3/1993
EP    0842122      8/2000
JP    7-328628     12/1995
WO    WO 99/20287  4/1999

OTHER PUBLICATIONS

Shirahata, Electrolyzed-reduced water scavenges active oxygen species and protects DNA from oxidative damage, Biochemical and Biophysics Research Communications, 1997, pp. 269-274, vol. 234, No. 1.
WPIDS abstract, accession No. 1996-096021, abstracting RU 2036662 (Jun. 1995), entry date of the abstract: Mar. 8, 1996.
Chemical Abstract 124:15556OK, Abstracting JP 7-328628 (Dec. 1995), Abstract Date: Mar. 1996.
VETU Abstract, Accession No. 1985-63045 (1985).
VETU Abstract, Accession No. 1988-60359 (1987).
VETU Abstract, Accession No. 1994-62049 (1994).
Kroschwitz, J.I. et al. (Eds.). Kirth-Othmer Encyclopedia of Chemical Technology, John Wiley & Sons, Inc., New York, 1994, vol. 9, pp. 124-140.
Peter Skaliy et al. "Laboratory Studies of Disinfectants Against *Legionella pneumophila*." *Applied & Environmental Microbiology*, Oct. 1980, vol. 40, No. 4, pp. 697-700. Published by CDC in Atlanta, GA.
Fraser, C.M. et al. (Eds.) The Merck Veterinary Manual, Merck & Co., Inc. (NJ), 1991, pp. 190, 1529-1531.

* cited by examiner

*Primary Examiner*—John Pak
(74) *Attorney, Agent, or Firm*—Fellers, Snider, Blankenship, Bailey & Tippens, P.C.; Dennis D. Brown

(57) ABSTRACT

This invention relates to a composition for use in the treatment of pathogenic microorganisms in a live animal, the composition comprising an electro-chemically activated, anion-containing aqueous solution.

9 Claims, No Drawings

USE OF AN AQUEOUS SOLUTION IN THE TREATMENT OF LIVE ANIMALS

RELATED APPLICATIONS

This is a continuation of U.S. patent application Ser. No. 10/679,449, filed Oct. 7, 2003, now abandoned which is a continuation-in-part of U.S. application Ser. No. 09/529,734, filed on Jun. 19, 2000, now abandoned, which was a 371 of international application No. PCT/US98/22372, filed Oct. 23, 1998, which claims priority to South African Patent Application Serial No. 97/9486, filed Oct. 23, 1997.

FIELD OF THE INVENTION

This invention relates to the use of an aqueous solution in the preparation of a medicament for use in the treatment of live animals. More particularly, the invention relates to a remedy for improving the growth performance of pigs and poultry, and to a method of treatment pigs and poultry to enhance their growth performance.

BACKGROUND OF THE INVENTION

For the purposes of this specification, the term "animal" should be construed to include within its meaning sheep, cattle, goats, pigs, chickens, ostriches, reptiles and the like; the term "disease" should be construed to include within its meaning diarrhoea; the term "pathogen" should be construed to include within its meaning microorganisms such as E-coli; and the term "medicament" should be construed to include within its meaning oral bactericides and bactericidal inhalants. The applicant envisages that the invention will be applicable particularly, but not exclusively, in the preparation of a medicament for use in the treatment of pathogenic microorganisms in weaner piglets and chicklets.

It will be appreciated that in the commercial rearing of domestic livestock, notably in the pig and poultry industries, the growth performance of animals forms the basis of economic viability of an operation. A number of factors may influence such growth performance such as temperature, diet, stocking rates, general husbandry and notably the presence and level of harmful pathogenic microorganisms. The microorganisms may be abundant in the water, food and in air space in which the animals are housed. In general, all pathogenic microorganisms exert a deleterious effect on the animal to a greater or lesser degree. This depends on factors such as the number of microorganisms present, the pathogenicity of the strain and its resistance to anti-microbials utilized in its control, as well as the immune status of an individual animal to a specific microorganism at any particular stage.

Methods such as antimicrobial medication of feeding rations, water treatment and inoculations are commonly employed to reduce the severity of impact on the animal.

The efficacy of a chosen control measure, or combination of measures, is gauged in general by the percentage reduction in mortalities and the growth rate of survivors, taking into account the efficacy of growth (i.e. the amount of feed consumed per unit of growth). This is referred to as the feed conversion rate.

The current methods for the control of microorganisms is based on low level, and sometimes therapeutic, medication of feeding rations, as well as drinking water consumed by the animal. This practice has fallen out of favour in recent times due to the resistance being built up by microorganisms to antibiotics, as well as residue levels of such agents in meat consumed by people. The presence of antibiotic residues in food products leads to allergic and anaphylactic reactions in humans. The development of resistant strains of microorganisms makes anti-microbials ineffective. This method of disease control was recently banned in the European Union and other countries are following suit.

SUMMARY OF THE INVENTION

It is accordingly an object of the invention to provide inexpensive, novel and alternative antimicrobials that overcome the above disadvantages.

It is a further object of the present invention to provide a growth promoting remedy suitable for use in enhancing growth performance in animals, and in particular in pigs and poultry.

It is another object of the invention to provide a method of treating animals, and in particular pigs and poultry, to promote their growth over any fixed period of time.

It is a further object of the invention to disinfect contaminated water in animal production farms so that the water in effect becomes a disinfecting agent.

According to a first aspect of the invention there is provided a composition for treating live animals, and particularly pigs and poultry, characterised therein that it treats pathogenic microorganisms, while at the same time enhancing growth performance in the animals, the composition comprising an electrochemically activated aqueous solution including separable and both of an aqueous, mixed oxidant, predominantly anion-containing solution and an aqueous, mixed anti-oxidant, predominantly cation-containing solution, the electrochemically activated aqueous solution being characterised therein that it is produced by an electrochemical reactor including a through-flow, electrochemical cell having two co-axial cylindrical electrodes with a co-axial diaphragm between the electrodes so as to separate an annular interelectrode space into a cathodic and an anodic chamber.

According to another aspect of the invention there is provided a method of treating live animals, and in particular pigs and poultry, so as to treat pathogenic microorganisms, while at the same time enhancing growth performance in the animals, the method comprising the steps of electrochemically activating an aqueous solution such that the solution includes separable and both of an aqueous, mixed oxidant, predominantly anion-containing solution and an aqueous, mixed anti-oxidant, predominantly cation-containing solution; separating the aqueous, mixed anti-oxidant, predominantly cation-containing solution from the aqueous, mixed oxidant, predominantly anion-containing solution; and introducing the aqueous, mixed anti-oxidant, predominantly cation-containing solution and the aqueous, mixed oxidant, predominantly anion-containing solution either simultaneously or sequentially into drinking water of the animal.

The anion-containing solution is referred to hereinafter for brevity as the "anolyte solution" or "anolyte" and the cation-containing solution is referred to hereinafter for brevity as the "catholyte solution" or "catholyte".

The anolyte is introduced into the drinking water at between 5% and 20%, and preferably 15% by volume. The catholyte is used as the drinking water dosed at a rate equivalent to between 5 ml and 20 ml, and preferably an average of 10 ml per kilogram bodyweight of the animals to be treated.

It is well known that animals are also infected via the oral route by the ingestion of infected litter, harbouring very high counts of pathogenic microorganisms. These particular pathogenic microorganisms enter the oral cavity and migrate towards the small intestine over a period of time. The applicant has found that introducing the predominantly anion-containing solution into the drinking water destroys these pathogenic microorganisms. Such a method prevents the microorganisms from migrating to the small intestine. The applicant refers this to as the "pre-pyloric" method of control as opposed to the traditional post-pyloric method utilized when medicating with antibiotics in food or drinking water.

The applicant utilized a cylindrical electrolytic device, having at least one electrolytic cell, in which the anodic and cathodic chambers are separated by a permeable membrane and the specific design of which permits the harnessing of two distinct, separate and electrochemically different product streams of activated water, in a process known as electrolytic activation (EA) or electrochemical activation (ECA).

The design of the specific cell utilized by the applicant for this invention is such as to ensure a uniformly high voltage electrical field through which each micro-volume of water must pass. This electric field created in the cylindrical cell has a high potential gradient and results in the creation of solutions of which the pH, oxidation reduction potential (ORP) and other physico-chemical properties, lie outside of the range that can normally be achieved by conventional chemical or most electrolytic means.

Two separate streams of activated solutions are produced, namely anolyte and catholyte. Depending on the production methods used and conditions of operation of the device, the anolyte typically can have a pH range of 1.5 to 9 and an oxidation-reduction potential (ORP) of +150 mV to +1200 mV. The anolyte is oxidizing, due to the presence of a mixture of oxidizing free radical ions, and has an antimicrobial effect. The catholyte typically can have a pH range of 8.5 to 13 and an ORP of about −150 mV to −900 mV. The catholyte has reducing and surfactant properties and is an antioxidant. Through experimentation the applicant has found that for the treatment of live animals, the anolyte should have a pH range of between 5.3 and 8.0 and an oxidation-reduction potential (ORP) in excess of +750 mV, while the catholyte should have a pH range of between 8.5 and 11 and an ORP of less than 600 mV.

One of the advantages of the design of the specific cell utilized by the authors for this invention is that the chemical composition of the two solutions can be altered by utilizing various hydraulic flow arrangements, linking electrolytic cell modules in various configurations in order optimally to address the requirements of specific areas of application. Some other variables are flow rate, hydraulic pressure, concentration, temperature, current density, and voltage on the electrodes.

Aside from its distinctive attributes, the catholyte can also be channeled back into the anode chamber, thereby modulating the quality of the anolyte that is produced. Depending on the specifications of the required application, variations in the design of the hydraulic systems can be effected to meet the requisite objectives.

The properties of electrolytically activated solutions are dependent upon a number of factors, including solution flow rate through the cell, type of salt used, voltage and current being applied, temperature, inter-flow dynamics of the solutions between the anode and cathode chambers, such as the degree of feedback of catholyte into the anolyte chamber, the design and geometry of the cell and the degree of mineralisation of the water.

It is important to note that the level of mineralisation of input water required to generate optimally formulated solutions is insignificantly different from the composition of potable water. However, the heightened electrical activity and altered physico-chemical attributes of the solutions differ significantly from the inactivated state, yet they remain non-toxic to animal tissue. Without maintenance of the activated state, these diverse products degrade to the relaxed state of benign water and the anomalous attributes of the activated solutions such as altered conductivity and surface tension similarly revert to pre-activation status.

The applicant believes that increased growth performance is achieved because of a reduction or elimination of pathogenic microorganisms present in water, food and in the environment surrounding the animal. The applicant has found that water medication at levels of as low as 0.1% anolyte reduces the presence of pathogenic microorganisms contained in it, thus reducing the risk of the animal becoming infected by this route.

The anion-containing aqueous solution may be prepared by means of electrolysis of an aqueous solution of a salt. The salt may be sodium chloride. In particular, it may be non-iodated sodium or potassium chloride, carbonates, bicarbonate, sulphate or phosphate, electrolysed to produce radical cation and radical anion species. These species may be labile and after about 96 hours, the various radical species may disappear with no residues being produced.

The anolyte solution may have a pH of between 5.3 and 7.5. The anolyte solution may include species such as ClO; ClO$^-$; HClO; OH$^-$; HO$_2^-$; H$_2$O$_2$; O$_3$; S$_2$O$_8^{2-}$; and Cl$_2$O$_6^{2-}$. These species have been found to have a synergistic anti-bacterial and/or anti-viral effect, which is generally stronger than that of chemical bactericides and has been found to be particularly effective against viral organisms and spore and cyst forming bacteria. The redox potential of the anolyte solution may be monitored during the process so that the treatment process may be monitored and controlled on a continuous basis.

The catholyte solution may include species such as NaOH; KOH; CA(OH)$_2$; Mg(OH)$_2$; HO$^-$; H$_3$O$_2^-$; HO$_2^-$; H$_2$O$_2^-$; O$_2^-$; OH$^-$; and O$_2^{2-}$.

The method of treatment may include administering the anolyte solution by soaking, rinsing or dipping the animal in the anolyte solution, or applying the anolyte solution as an inhalant via an atomising or fogging process. The soaking, rinsing or dipping process is suitable for animals that can be handled with relative ease.

The method of treatment may include a method of treating a nonhuman live animal susceptible to becoming diseased as a result of exposure to pathogenic microorganisms, said live animal having a digestive system and said pathogenic microorganisms being present in an environment of said live animal in any manner such that said pathogenic microorganisms will enter and become present in said digestive system, said method comprising the step of orally administering to said live animal an aqueous, anion-containing, anolyte product solution produced by electro-chemical activation of an aqueous solution of a salt selected from the group consisting of sodium chloride and potassium chloride such that said anolyte product solution has an oxidation-reduction potential in the range of from about $^+$600 mV to about $^+$800 mV and a pH in the range of from about 6.5 to about 7.5, said anolyte product solution being orally administered to said live animal by adding an effective amount of said anolyte product solution to the animal's drinking water for 7 or more days and having the animal drink the combined drinking water and said anolyte production solution for said 7 or more days in an amount sufficient to destroy said pathogenic microorganisms which enter and become present in said digestive system.

The processes of atomising or fogging and oral administration by addition to drinking water are both suitable for animals such as weaner piglets and chicklets, which are susceptible to stress and accompanying weight loss. The atomising or fogging process may include the step of atomising the solution into the atmosphere in a volume to be treated, forming droplets of up to 100 micrometer. The method may include the preliminary step of enclosing the volume to be treated prior to atomising or fogging the enclosed volume.

The atomising or fogging process is preferably conducted at pre-determined intervals so as to maintain a suitable level of anolyte concentration in the atmosphere, thus utilising the optimum microcidal and other properties of the anolyte solution in accordance with the required administration rate.

The anolyte solution may also be applied by an atomising process in air ducting systems to destroy air-borne microorganisms and to destroy microorganisms present in the airways and lung tissue by inhalation.

The treatment of the animal as described above may be conducted so as to improve the weight gain as a result of the anti-microbial action of the anolyte solution.

The anolyte solution may have a specific anion concentration and distribution and a redox potential in accordance with the specific application.

The pathogenic microorganisms to be treated may include enteric pathogenic microorganisms and respiratory pathogenic microorganisms.

DETAILED DESCRIPTION OF THE PREFERRED EMBODIMENT

A preferred embodiment of the invention will now be described with reference to the accompanying experiments.

In a series of experiments, the bactericidal effect of the anolyte solution was tested on animals. The results are reflected in the tables below.

The basic electrolytic cells used to generate the electrolytically activated solutions utilized in this invention are modular units with the operational specifications for the reactors being optimised for each specific application. The cell includes a cylindrical metal vessel typically about 210 mm long and 16 mm in diameter, having a central rod anode (positive electrode) located within a concentric ceramic tube membrane. The outer tubular wall of the cell reactor acts as the cathode (negative electrode). Provision is made for inlet and outlet ports for the passage of the fluid through it.

Effectively, the ceramic membrane divides the cell into two compartments, the anode compartment and the cathode compartment. Water enters the cell and exits from these compartments as two streams, namely the anolyte and the catholyte, respectively. If so desired, some or all of the catholyte may be returned to the anode compartment so as to vary the properties of the anolyte being produced. Similarly, some or all of the anolyte may be returned to the cathode compartment so as to vary the properties of the catholyte being produced. A number of other hydraulic system configurations also exist, all of which are designed to achieve specific objectives.

The design of the cell is such as to ensure a very high uniform electric field through which each micro volume of water must pass. In so doing the molecules of water in the anolyte and catholyte acquire special properties which cannot be reproduced by other (more conventional chemical) means. This electrolytic treatment results in the creation of anolyte and catholyte solutions whose pH, oxidation-reduction potentials (ORP) and other physico-chemical properties lie outside of the range that can be achieved by conventional chemical means.

In this invention the pH, ORP and concentration values of chlorine, chlorides and other dissolved salts have been determined, unless otherwise stated, as per standard methods of examination of water and effluents.

EXAMPLE 1

Weaner Piglets

The anolyte solution was added to the drinking water of the weaner piglets over a period of 14 days and the results were measured in terms of average weight after the 14 day period. The average weight of the administered groups were compared with the average weight of the non-administered groups.

The administered groups showed relative weight gain relative to the non-administered groups.

EXAMPLE 2

Broilers (Chicklets)

Day old broilers were administered with anolyte solution (10% diluted) by addition to drinking water for 7 days. (Group C3—12,000 chicklets). No antibiotic medication was administered during that time. Untreated control groups (C1, C2, C4 and C5=total 48,000 chicklets) received normal drinking water during that time. The untreated groups were routinely medicated with Tylosin for 3 consecutive days.

Bacterial analyses of the drinking water of all groups were regularly conducted during the first 7 days. Other measurements included daily mortalities and morbidities throughout and pH and ORP determinations of the drinking water during the first 7 days.

Medication of drinking water with anolyte solution supplied to day-old chicklets for the first period resulted in a significant reduction in mortalities throughout the growth and finishing period. Mortalities increased in all the groups from the 4th week onwards mainly due to respiratory disease. It is envisaged that these could be reduced by fogging the environment with anolyte solution to eliminate airborne respiratory pathogens by means of respiratory intake.

It has been found that the efficacy of the use of the anolyte solution in the treatment of live animals depends upon the concentration of the anions in the anolyte solution, as measured by the oxidation-reduction potential (ORP) or redox potential of the anolyte solution, the flow rate through the reactor, the exposure time, i.e. the contact time between the contaminated animal and the anolyte solution and the temperature during application. By measuring the redox potential of the anolyte solution during the treatment, for example, of a weaner piglet, the available free radical concentration can be monitored. Anolyte solution has been found to be more effective at lower than at higher temperatures.

EXAMPLE 3

Broilers (Chicklets)

The applicant has found that growth rates in broiler chickens were significantly enhanced when the water source was treated with anolyte when compared to an untreated control group. The trial consisted of one control group and six treatment groups, each with three replicates of 50 chickens. All replicates were randomly assigned a trial enclosure within the same house, and all chickens were hatched on the same day from the same parent flock. Weight recordings were conducted every second week on the total group and on alternate weeks on individual chickens. All mortalities were recorded. Feed and water were supplied ad libitum and feed intake per replicate accurately recorded. The following treatments were applied:

| Control group | Received no medication in water |
|---|---|
| Oxine | water medication for 42 days |
| Chemsol | water medication for 42 days |
| Anolyte (10%) | water medication for 42 days |
| Anolyte (15%) | water medication for 12 days |
| Anolyte (20%) | water medication for 12 days |

Chickens were slaughtered at 42 days, at which time final live weights and food intake over the period recorded.

The following table summarizes the results (i.e. weight in grams):

| MEDICATION | DAY 0 | DAY 7 | DAY 14 | DAY 21 | DAY 28 | DAY 35 | DAY 35 |
|---|---|---|---|---|---|---|---|
| Control | 39.0 | 90.6 | 129.7 | 441.2 | 795.2 | 1284.7 | 1903.4 |
| Oxine | 39.3 | 94.7 | 200.3 | 461.7 | 815.5 | 1346.2 | 1955.9 |
| Chematron | 40.7 | 118.0 | 259.2 | 571.0 | 960.0 | 1495.2 | 2119.0 |
| 10% Anolyte | 40.0 | 126.9 | 278.0 | 603.4 | 1031.8 | 1592.6 | 2227.8 |
| 15% Anolyte | 40.0 | 130.7 | 294.8 | 631.3 | 1061.6 | 1650.7 | 2283.3 |
| 20% Anolyte | 40.0 | 125.3 | 283.7 | 579.9 | 1006.0 | 1572.3 | 2106.8 |

EXAMPLE 4

Broilers (Chicklets)

Production parameters (as measured by mortality reduction, final slaughter mass, kilogram meat produced per $m^2$ floor space and feed conversion rates) in the following example were significantly enhanced. In this trial the above parameters obtained on the same site in 2 previous cycles (i.e. 110 and 111) were compared to the experimental one (i.e. 112) where broiler chickens were again treated with anolyte. The site consisted of 6 broiler houses each stocked with 2700 broilers.

| CYLE NO. | AVE. FLOCK AGE | MORTALITY % | AVE AGE | AVE MASS (KG) | KG/$M^2$ PER HOUSE | FEED CONVERSION RATE |
|---|---|---|---|---|---|---|
| 110 | 37.1 | 6.01 | 39.5 | 1.805 | 30.97 | 1.88 |
| 111 | 37.1 | 9.09 | 39.0 | 1.741 | 29.23 | 1.92 |
| 112 | 36.6 | 5.25 | 40.9 | 2.006 | 35.07 | 1.86 |

It is evident from the above results that when the anionic solution was dosed into the drinking water at an inclusion rate of 15%, fewer chickens died, the live mass was significantly higher whilst converting food more efficiently. In this trial approximately 5 kg live mass per square meter floor space, equating to 7.35 tonnes per house or 44.1 tonnes per site additional meat, was produced. No antibiotic water medication was employed in cycle 112 whilst in both preceding cycles FOSBAC (fosamycin 20% and tylosin 5%) was used.

EXAMPLE 5

Weaner Piglets

In this trial the effect of the addition of anolyte on the productivity of weaners was studied. The trial was carried out over two rounds with a total of 16 replicates per round and 400 pigs per group. Microbial examinations of drinking water showed the total number of bacteria to be reduced from 3,500,000/ml to zero and of Coliforms from >160/ml to zero when either 25% or 10% anolyte was added. Mortalities and clinical cases showed no difference between treatment and control groups.

The following table summarizes results:

| GROUP | CONTROL | ANOLYTE |
|---|---|---|
| Number of pens | 16 | 16 |
| Number of pigs penned | 408 | 408 |

-continued

| GROUP | CONTROL | ANOLYTE |
|---|---|---|
| Daily gain (g) - first 2 weeks post weaning | 116 | 141 |
| Daily feed intake - first 2 weeks post weaning (kg) | 0.22 | 0.24 |
| Feed conversion (kg feed/kg gain) | 1.94 | 1.72 |

It will be appreciated that many variations in detail are possible without departing from the scope and/or spirit of the invention as set out in the claims hereinafter.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A method of treating a nonhuman live animal susceptible to becoming diseased as a result of exposure to pathogenic microorganisms, said live animal having a digestive system and said pathogenic microorganisms being present in an environment of said live animal in any manner such that said pathogenic microorganisms will enter and become present in said digestive system, said method comprising the step of orally administering to said live animal an aqueous, anion-containing, anolyte product solution produced by electrochemical activation of an aqueous solution of a salt selected from the group consisting of sodium chloride and potassium chloride such that said anolyte product solution has an oxidation-reduction potential in the range of from about $^+600$ mV to about $^+800$ mV and a pH in the range of from about 6.5 to about 7.5, said anolyte product solution being orally administered to said live animal by adding an effective amount of said anolyte product solution to the animal's drinking water for 7 or more days and having the animal drink the combined drinking water and said anolyte production solution for said 7 or more days in an amount sufficient to destroy said pathogenic microorganisms which enter and become present in said digestive system.

2. The method of claim 1 wherein said anolyte product solution comprises: ClO; ClO$^-$; HClO; OH$^-$; HO$_2^-$; H$_2$O$_2$; O$_3$; S$_2$O$_8^{2-}$; Cl$_2$O$_6^{2-}$; or a combination thereof.

3. The method of claim 1 wherein said pathogenic microorganisms comprise an enteric micro-organism.

4. The method of claim 1 wherein said pathogenic microorganisms comprise viral organisms.

5. The method of claim 1 wherein said pathogenic microorganisms comprise bacterial spores.

6. The method of claim 1 wherein said pathogenic microorganisms comprise cyst forming bacteria.

7. The method of claim 1 wherein said pathogenic microorganisms comprise *E-coli*.

8. The method of claim 1 wherein said anolyte product solution is added to said animal's drinking water in an amount such that said anolyte product solution comprises 10% by volume of the total combined volume of said drinking water and said anolyte product solution.

9. The method of claim 1 wherein said amount sufficient to destroy said pathogenic microorganisms is also an amount effective to cause an increased weight gain of said live animal.

* * * * *